United States Patent [19]

Stampa Díez Del Corral et al.

[11] Patent Number: 5,426,227
[45] Date of Patent: Jun. 20, 1995

[54] ENANTIOSELECTIVE PROCESS FOR THE PREPARATION OF LEVEOBUNOLOL

[75] Inventors: Alberto Stampa Díez Del Corral; Pelayo Camps García; Maria del Carmen Onrubia Miguel, all of Barcelona; Carmen Arnalot Aguilar, Gerona, all of Spain

[73] Assignee: Medicham, S.A., Barcelona, Spain

[21] Appl. No.: 213,945

[22] Filed: Mar. 16, 1994

[30] Foreign Application Priority Data

Jun. 24, 1993 [ES] Spain ........................ 9301422

[51] Int. Cl.$^6$ ........................................... C07C 213/02
[52] U.S. Cl. ........................................................ 564/349
[58] Field of Search ........................................... 564/349

[56] References Cited

U.S. PATENT DOCUMENTS

| | | | |
|---|---|---|---|
| 3,641,152 | 2/1972 | Shavel, Jr. et al. | 564/349 |
| 3,649,691 | 3/1972 | Shavel, Jr. et al. | 564/349 |
| 4,463,176 | 7/1984 | Dennis et al. | 546/208 |
| 4,849,527 | 7/1989 | Dennis et al. | 548/507 |

FOREIGN PATENT DOCUMENTS 4133143 4/1993 Germany .

OTHER PUBLICATIONS

McClure et al. (1979) "Mode of Nucleophilic Addition to Epichlorohydrin and Related Species: Chiral Aryloxymethyloxiranes", *JACS*, 101:3666–3668.

Ohishi et al. (1983) "Reaction of Epichlorohydrin with Hydroxybenzo[b]furan", *Chem. Pharm. Bull.*, 31:3418–3423.

Schwender et al. (1970) "Derivatives of 3,4-Dihydro-1(2H)-naphthalenone as β-Adrenergic Blocking Agents. 1 Bunolol and Related Analogs", *J. Medical Chemistry*, 13:684–688.

*Primary Examiner*—Richard L. Raymond
*Attorney, Agent, or Firm*—Scully, Scott, Murphy & Presser

[57] ABSTRACT

The invention relates to a new, industrially advantageous, process for the preparation of the known beta-adrenergic blocking agent, levobunolol, not requiring resolution of racemic bunolol, based on the enantioselective synthesis of an oxiranic intermediate which is then reacted with tert-butylamine. It consists of reacting 5-hydroxy-3,4-dihydro-1(2H)-naphthalenone with (R)-(-)epichlorhydrine in an aprotic solvent, in the presence of a strong base at a temperature of over 90° C., thus obtaining the intermediate chiral oxirane (S)-5-(2,3-epoxypropoxy)-3,4-dihydro-1-(2H)-naphthalenone with more than 95% optical purity, and then, the intermediate chiral oxirane is reacted with tert-butylamine.

6 Claims, No Drawings

ENANTIOSELECTIVE PROCESS FOR THE PREPARATION OF LEVEOBUNOLOL

FIELD OF THE INVENTION

This invention relates to a new process for the preparation of the drug levobunolol, a known beta-adrenergic blocking agent, in which the configuration of the chiral center is established through enantioselective synthesis.

PRIOR ART

Levobunolol is the levorotatory enantiomer of bunolol, 5[3-(tert-butylamino)-2-hydroxypropoxy]-3,4-dihydro-1(2H)-naphthalenone, having the structural formula:

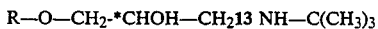

R—O—CH$_2$—*CHOH—CH$_2$13 NH—C(CH$_3$)$_3$ in which, R is 3,4-dihydro-1-oxo-(2H)-naphthalen-5-yl and the chiral center has been denoted by an asterisk. More specifically, levobunolol, (S)-(-)-5-[3-(tert-butylamino)-2-hydroxypropoxy]-3,4-dihydro-1(2H)-naphthalenone, has the following spatial formula

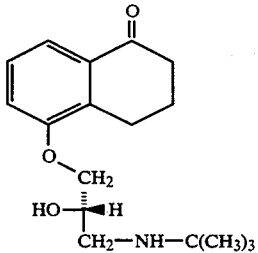

having the S configuration for the chiral center which, according to U.S. Pat. No. 3,649,691 (Shavel, J. et al.), shows a beta-adrenergic blocking activity sixty times greater than its R enantiomer, and twice that of the racemic mixture.

Thus, the preferred industrial interest lies in the preparation of the S enantiomer. To this end, fractional crystallization of diastereomeric salts of racemic bunolol and D-(-)-tartaric and L-(+)-tartaric acids has been proposed (Charles F. Schwender et al., J. Med. Chem., 1970, 13, 684). Moreover, U.S. Pat. Nos. 4,463,176 (Dennis et al.) and 4,849,527 (Dennis at al.) describe the conversion of racemic bunolol into a diastereomeric mixture of urea-derivatives by reacting it with a chiral isocyanate. After separation of the diastereomeric urea-derivatives, optically active levobunolol is obtained from the appropriate urea by reaction with hydrazine.

U.S. Pat. No. 3,641,152 (Shavel et al.) teaches the preparation of racemic bunolol by reacting first, 5-hydroxy-3,4-dihydro-1(2H)-naphthalenone with epichlorhydrine, and then, reacting the intermediate epoxide with tert-butylamine.

Up to now, no process has been described for the preparation of levobunolol based on the enantioselective synthesis of the required oxiranic intermediate, through the reaction of 5-hydroxy-3,4-dihydro-1(2H)-naphthalenone with the appropriate enantiomer of epichlorhydrine, in such a way that the reaction of this oxiranic intermediate with tert-butylamine gives levobunolol directly.

The reaction of a phenol with epichlorhydrine, as it is described in Chem. Pharm. Bull., 1983, 31, 3418 (Oshishi et al.) can proceed through two different mechanisms: one, denoted as route a, by direct substitution of the chlorine atom of epichlorhydrine, and another, denoted as route b, by nucleophilic attack of the phenoxide ion on the oxiranic carbon atom followed by elimination of chloride ion. When this reaction is carried out with racemic epichlorhydrine, it does not matter which route is followed by the reaction since in both cases the racemic oxirane intermediate is formed. However, if one enantiomer of epichlorhydrine is used to obtain one of the enantiomers of the intermediate oxirane, routes a and b each give a different enantiomer and, where there is no preference for one of these routes, an at least partially racemized intermediate is obtained. In Scheme 1, the possible formation of both enantiomers of the intermediate oxirane as a function of the mechanism of the reaction (routes a and b), is shown.

Scheme 1

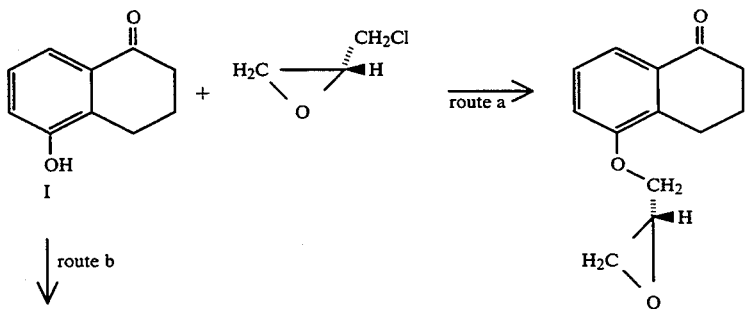

Scheme 1

-continued

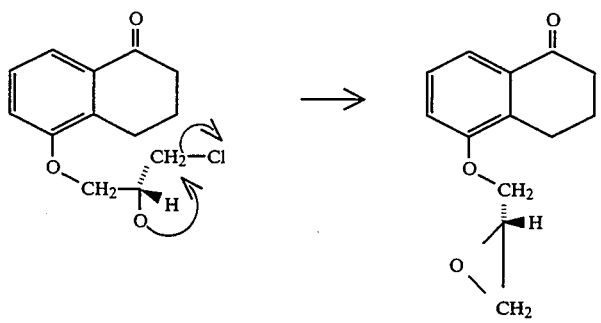

According to the work of Ohishi et al., this reaction shows a slight preference for route b.

Moreover, McClure et al. (J. Amer. Chem. Soc., 1979, 101, 3666), describe the reaction of different phenolic compounds with both enantiomers of epichlorhydrine. Particularly, they proposed two processes for the preparation of the corresponding aryloxymethyloxiranes: in one of them, the reaction of the phenolic compound and chiral epichlorhydrine is carried out in acetone or methylene chloride under reflux in the presence of potassium carbonate, in the other one, chiral epichlorhydrine is reacted with the previously prepared phenoxide in dimethylformamide as solvent. According to the reported results, the process that uses acetone and potassium carbonate shows some preference for route b. However, some erratic values were observed and, in no case, were the optical purities greater than 95%.

For an enantioselective process of preparation of levobunolol to be industrially adequate and more advantageous than those previously described, the reaction of 5-hydroxy-3,4-dihydro-1(2H)-naphthalenone with one of the enantiomers of epichlorhydrine must provide a product of more than 95% optical purity in a stable and repetitive way. Otherwise, the process loses worth and efficacy since purification of levobunolol of low optical purity requires the use of racemic separation techniques, i.e. selective crystallization of diastereomeric salts with D- and L-tartaric acids, such as those industrially expensive and not very appropriate techniques described by Charles F. Schwender, and mentioned above.

The present invention overcomes all these problems and, for the first time, describes an industrially advantageous and efficient process for the enantioselective preparation of levobunolol, that does not need the use of the expensive techniques of resolution of racemic bunolol based on the formation of diastereomeric salts or diastereomeric derivatives of the end product.

SUMMARY OF THE INVENTION

The object of the present invention is a new, industrially advantageous, process for the preparation of levobunolol, not requiring the resolution of racemic bunolol, based on the enantioselective synthesis of the intermediate oxirane (S)-5-(2,3-epoxypropoxy)-3,4-dihydro-1(2H)-naphthalenone, in high chemical yield and optical purity, followed by reaction with tert-butylamine.

DETAILED DESCRIPTION OF THE INVENTION

The process of the present invention consists of:

i) reacting 5-hydroxy-3,4-dihydro-1(2H)-naphthalenone with (R)-(-)-epichlorhydrine, in an aprotic solvent in the presence of a strong base at a temperature of over 90° C., to give the intermediate chiral oxirane (S)-5-(2,3-epoxypropoxy)-3,4-dihydro-1(2H)-naphthalenone with an optical purity greater than 95%, and then, ii) reacting the intermediate chiral oxirane with tert-butylamine.

The sequence of chemical reactions that comprise the process of the present invention is shown in Scheme 2. 5-Hydroxy-3,4-dihydro-1(2H)-naphthalenone (I) is reacted with (R)-(-)-epichlorhydrine [(R)-II] to give the intermediate [(S)-III] which, by reaction with tert-butylamine gives levobunolol [(S)IV].

Scheme 2

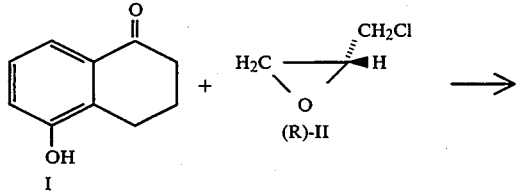

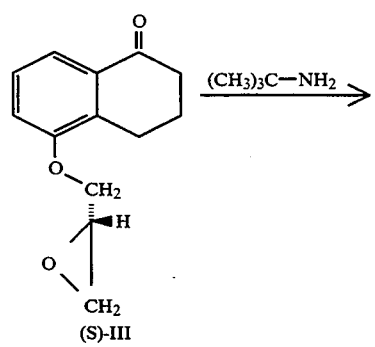

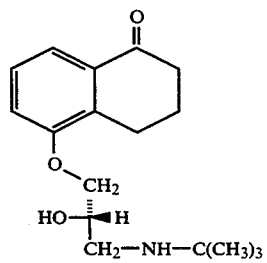

Appropriate solvents for the first step of the process of the present invention are, among others, benzene, toluene, xylene, dimethoxyethane, diglyme, 1,4-dioxane, etc., toluene being especially preferred.

In this step, alkaline or alkaline earth metal, such as potassium, sodium or calcium, hydroxides can be used as strong base.

For high optical purities, the reaction of 5-hydroxy-3,4-dihydro-1(2H)-naphthalenone and (R)-(-)-epichlorhydrine must be carried out at temperatures of over 90° C.

In order to favour the first step of the synthesis, a phase-transfer catalyst may be used, i.e., benzyltriethylammonium chloride, methyltricaprylammonium bromide, tetra-n-butylammonium bromide, etc.

The reaction time is not particularly critical, the formation of the intermediate chiral oxirane being completed in a period of one to ten hours.

The second step, i.e., the reaction of the intermediate chiral oxirane (S)-5-(2,3-epoxypropoxy)-3,4-dihydro-1-(2H)-naphthalenone and tert-butylamine is carried out following standard processes, such as heating these reactants under reflux in an alcoholic solvent.

If desired, the thus obtained levobunolol can be converted into any of the appropriate salts for pharmaceutical use, such as the hydrochloride.

The two steps of the process of the present invention, and the optional conversion of levobunolol into its hydrochloride, can be carried out without isolating the intermediates, thus greatly simplifying the industrial implementation of this process.

Surprisingly, in spite of the uncertainty and low optical purities described by McClure et al. in the case of other phenolic compounds, the new process of this invention gives levobunolol in high optical purity, in an industrially repetitive way which has remarkable advantages of simplicity and costs with respect to the previously known processes for the preparation of this product.

For a better understanding of the process of the present invention, the following example is given, without restrictive value:

EXAMPLE 9.62 g (59 mmoles) 5-hydroxy-3,4-dihydro-1(2H)-naphthalenone, 67 ml toluene, 0,36 g (1.1 mmoles) tetra-n-butylammonium bromide, 4.51 g (68 mmoles) 85% potassium hydroxide and 20 ml (254 mmoles) (R)-(-)-epichlorhydrine were placed in an appropriate flask fitted with efficient mechanical stirring, and the mixture was heated under reflux for two hours. The mixture was allowed to cool to 30° C., 50 ml toluene and 50 ml water were added and the mixture was vigorously stirred. The organic phase was removed and the aqueous phase extracted with 25 ml toluene.

The combined organic phases were concentrated at reduced pressure, 31 ml (300 mmoles) tert-butylamine, 45 ml ethanol and 3 ml deionized water were added, and the solution was heated under reflux for one hour. The mixture was allowed to cool to 40° C. and the volatile products were distilled at reduced pressure. Toluene (9 ml) was added to the residue and volatiles were distilled at reduced pressure.

Toluene (75 ml) was added to the residue, and then, 10 ml of 35% (w/v) hydrochloric acid and 110 ml water, and the mixture was stirred for fifteen minutes. The organic phase was decanted and the aqueous one was extracted with 50 ml toluene. The aqueous phase was basified by addition of a solution of 5.1 g sodium hydroxide in 150 ml water and extracted twice with toluene (100 and 50 ml, respectively). The combined organic extracts were dried with anhydrous sodium sulphate, decolorized with active charcoal and filtered.

To the above toluenic solution containing levobunolol as free base, 16 ml ethanol and the stoichiometric amount of hydrogen chloride were added. The stirred mixture was cooled below 10° C. and kept at this temperature for one hour. The precipitated solid was filtered, washed with toluene, recrystallized twice from 43 ml ethanol and dried to give 10.0 g (51% yield) of levobunolol hydrochloride having a rotary power at 25° C. below −19°.

What we claim is:

1. Enantioselective process for the preparation of the levobunolol, (S)-(-)-5-[3-(tert-butylamino)-2-hydroxypropoxy]-3,4-dihydro-1(2H)-naphthalenone, comprising the following steps:
   i) reacting 5-hydroxy-3,4-dihydro-1(2H)-naphthalenone with (R)-(-)-epichlorhydrine in an aromatic hydrocarbon solvent in the presence of a strong base at a temperature of over 90° C., to give, the intermediate chiral oxirane (S)-5-(2,3-epoxypropoxy)-3,4-dihydro-1-(2H)-naphthalenone with an optical purity greater than 95% and then,
   ii) reacting the intermediate chiral oxirane with tert-butylamine.

2. The process of claim 1 in which the strong base used is an alkaline or alkaline earth metal hydroxide.

3. The process of claim 1 in which the aromatic hydrocarbon solvent is benzene, toluene, or xylene.

4. The process of claim 1 in which a phase transfer catalyst is used in the first step.

5. The process of claim 4 in which the phase transfer catalyst is one of the group formed by benzyltriethylammonium chloride, methyltricaprylammonium chloride or tetra-n-butylammonium bromide.

6. The process of one of claims 1 to 4 in which the first step is carried out using toluene as solvent, potassium hydroxide as strong base, at the reflux temperature of the solvent for a time comprised between one and three hours.

* * * * *

UNITED STATES PATENT AND TRADEMARK OFFICE
CERTIFICATE OF CORRECTION

PATENT NO. : 5,426,227
DATED : June 20, 1995
INVENTOR(S) : Alberto Stampa Diez Del Corral, et al.

It is certified that error appears in the above-indentified patent and that said Letters Patent is hereby corrected as shown below:

Column 1, line 18: "R-O-$CH_2$-$^*$CHOH-$CH_2$13 NH-C$(CH_3)_3$" should read --R-O-$CH_2$-$^*$CHOH-$CH_2$-NH-C$(CH_3)_3$ --

Signed and Sealed this

Ninth Day of July, 1996

Attest:

BRUCE LEHMAN

Attesting Officer     Commissioner of Patents and Trademarks